US007965392B2

(12) United States Patent
Tamura

(10) Patent No.: US 7,965,392 B2
(45) Date of Patent: Jun. 21, 2011

(54) OPTICAL COHERENCE TOMOGRAPHY DEVICE AND MEASURING HEAD

(75) Inventor: Masami Tamura, Kyoto (JP)

(73) Assignee: Shofu Inc., Kyoto (JP)

( * ) Notice: Subject to any disclaimer, the term of this patent is extended or adjusted under 35 U.S.C. 154(b) by 317 days.

(21) Appl. No.: 12/087,846

(22) PCT Filed: Jan. 19, 2006

(86) PCT No.: PCT/JP2006/300719
§ 371 (c)(1),
(2), (4) Date: Jul. 16, 2008

(87) PCT Pub. No.: WO2007/083376
PCT Pub. Date: Jul. 26, 2007

(65) Prior Publication Data
US 2009/0021745 A1 Jan. 22, 2009

(51) Int. Cl.
*G01B 9/02* (2006.01)
*G01B 11/02* (2006.01)
(52) U.S. Cl. ........................................ 356/479; 356/497
(58) Field of Classification Search .................. 356/479, 356/497; 250/227.19, 227.27
See application file for complete search history.

(56) References Cited

U.S. PATENT DOCUMENTS

| 6,134,003 | A  | * | 10/2000 | Tearney et al. ............... 356/479 |
| 6,289,235 | B1 |   | 9/2001  | Webber et al. |
| 6,377,349 | B1 |   | 4/2002  | Fercher |
| 6,882,429 | B1 | * | 4/2005  | Weitekamp et al. ........... 356/482 |
| 6,973,844 | B2 | * | 12/2005 | Sakai ........................ 73/862.041 |
| 7,007,553 | B2 | * | 3/2006  | Kinoshita et al. ............... 73/777 |
| 2001/0034482 | A1 | | 10/2001 | Webber et al. |

(Continued)

FOREIGN PATENT DOCUMENTS

JP 11-325849 11/1999

(Continued)

OTHER PUBLICATIONS

Haruna, et al., "Technical Development of Optical Coherence Tomography for Clinical Application", Laser Review, Oct. 2003, pp. 654-662.

(Continued)

*Primary Examiner* — Michael A Lyons
(74) *Attorney, Agent, or Firm* — Hamre, Schumann, Mueller & Larson, P.C.

(57) ABSTRACT

An optical coherence tomography device includes: a light source 16; a light splitting section 19 that splits light source light into reference light 19 and measuring light 28 with which a sample 22 is irradiated; an interfering section 19 that allows the measuring light 28 to interfere with the reference light 29 to generate interference light; a photodetectiong section 26 that measures interference light; a movable measuring head 201 that changes the irradiating position and/or direction, irradiated with the measuring light 28, by a motion of the measuring head 20; a mechanical quantity sensor 38 that measures the motion of the measuring head 201; and an operating section 27 that obtains information on the sample 22, based on the interference light measured by a photodetectiong section 26 and the motion of the measuring head 201 measured by the mechanical quantity sensor 38. Thus, an optical coherence tomography device capable of capturing an image at a high speed with a simple structure can be provided.

4 Claims, 7 Drawing Sheets

U.S. PATENT DOCUMENTS

| | | |
|---|---|---|
| 2003/0048540 A1 | 3/2003 | Xie et al. |
| 2004/0085543 A1* | 5/2004 | Xie et al. ............ 356/479 |
| 2005/0113682 A1 | 5/2005 | Webber et al. |
| 2007/0165922 A1 | 7/2007 | Webber et al. |

FOREIGN PATENT DOCUMENTS

| | | |
|---|---|---|
| JP | 2001-59714 | 3/2001 |
| JP | 2001-174404 | 6/2001 |
| JP | 2002-505437 | 2/2002 |
| JP | 2002-82045 | 3/2002 |
| JP | 2002-310897 | 10/2002 |
| JP | 2003-329577 | 11/2003 |
| WO | 2004/085956 | 10/2004 |

OTHER PUBLICATIONS

Fried, et al., "Imaging caries lesions and lesion progression with polarization sensitive optical coherence tomography", Journal of Biomedical Optics, vol. 7, No. 4, Oct. 2002, pp. 618-627.

Colston, et al., "Imaging of hard- and soft-tissue structure in the oral cavity by optical coherence tomography", Applied Optics, vol. 37, No. 16, Jun. 1998, pp. 3582-3585.

Colston, et al., "Dental OCT", Optics Express, vol. 3, No. 6, Sep. 1998 pp. 230-238.

Feldchtein, et al., "In vivo OCT imaging of hard and soft tissue of the oral cavity", Optics Express, vol. 3, No. 6, Sep. 1998, pp. 239-250.

* cited by examiner

OPTICAL COHERENCE TOMOGRAPHY DEVICE AND MEASURING HEAD

TECHNICAL FIELD

The present invention relates to an optical coherence tomography (tomography using low coherent light as a probe) device that is one nondestructive tomography technique.

BACKGROUND ART

Conventionally, in the dental diagnosis, X-ray equipment, an intraoral camera, a dental camera, X-ray CT, MRI, etc. have been used for photographing a stomatognathic region.

An image obtained in the X-ray equipment is only a transmitted image, and information on an X-ray traveling direction of a subject is detected while being overlapped with each other. Therefore, the internal structure of the subject cannot be known three-dimensionally. Furthermore, an X-ray is harmful to a human body, so that an annual exposure dose is limited, and an X-ray is dealt with only by an eligible operator and is used only in a room surrounded by a shielding member of lead, lead glass, or the like.

The intraoral camera captures only the surface of an intraoral tissue, so that information on the inside of teeth and the like cannot be obtained. The X-ray CT is harmful to a human body in the same way as in the X-ray equipment. In addition, the X-ray CT has poor resolution, and the device is large and expensive. The MRI has poor resolution, and the device is large and expensive. In addition, the MRI cannot photograph the internal structure of teeth containing no moisture.

The optical coherence tomography device (hereinafter, referred to as an OCT device) is harmless to a human body, and enables three-dimensional information on a subject to be obtained with high resolution. Therefore, the optical coherence tomography device has been applied to the opthalmological field such as tomography of a cornea and a retina, etc. (see, for example, Patent Documents 1-4).

Hereinafter, a conventional OCT device will be described. FIG. 13 is a diagram showing a configuration of a conventional OCT device. In an OCT unit 1 constituting the OCT device shown in FIG. 13, light emitted from a light source 2 is collimated by a lens 3, and thereafter, is split into reference light 6 and measuring light 5 by a beam splitter 4. The measuring light 5 is condensed to a sample 10 to be measured by an objective lens 9 via a galvanomirror 8. Then, the condensed light is scattered and reflected from the sample 10, and passes through the objective lens 9, the galvanomirror 8, and the beam splitter 4 again to be condensed to a light photodetector 14 via a condensing lens 7. On the other hand, the reference light 6 passes through the objective lens 12 and is reflected from a reference mirror 13. Then, the reference light 6 passes through the objective lens 12 and the beam splitter 4 again, and thereafter is incident upon the condensing lens 7 in parallel with the measuring light 5 to be condensed to the photodetector 14.

The light source 2 is a low coherent in terms of time. Light beams emitted at different times from a light source that is low coherent in terms of time are very unlikely to interfere with each other. Therefore, an interference signal appears only when the distance of an optical path through which the measuring light 5 passes is substantially equal to that of an optical path through which the reference light 6 passes. Consequently, when the intensity of an interference signal is measured by the photodetector 14 while a difference in optical path length between the measuring light 5 and the reference light 6 is changed by moving the reference mirror 13 in an optical axis direction of the reference light 6, a reflectance distribution in a depth direction (z-axis direction) of the sample 10 can be obtained. That is, the structure in the depth direction of the sample 10 is obtained by optical path length difference scanning.

The two-dimensional cross-sectional image of the sample 10 is obtained by performing scanning in a horizontal direction (x-axis direction) by the galvanomirror 8 in addition to scanning in the depth direction (z-axis direction) of the sample to be measured by the reference mirror 13. In such an OCT device, measurement with resolution as high as several μm can be performed. Thus, the OCT device enables an image with high resolution of the inside of a living body to be obtained in a nondestructive and noncontact manner.

Regarding the application of the OCT device to the dental field, an example is disclosed in which a dental tomogram is taken using an OCT device (see, for example, Non-Patent Documents 1-5).

Patent Document 1: JP 2003-329577 A
Patent Document 2: JP 2002-310897 A
Patent Document 3: JP 11-325849 A
Patent Document 4: JP 2001-059714 A
Non-Patent Document 1: Laser review October, 2003: Technical development of optical coherence tomography for clinical application
Non-Patent Document 2: Journal of Biomedical Optics, October 2002, Vol. 7 No. 4: Imaging caries lesions and lesion progression with polarization sensitive optical coherence tomography
Non-Patent Document 3: APPLIED OPTICS, Vol. 37, No. 16, 1 Jun. 1998: Imaging of hard- and soft-tissue structure in the oral cavity by optical coherence tomography
Non-Patent Document 4: OPTICS EXPRESS, Vol. 3, No. 6, 14 Sep. 1998: Dental OCT
Non-Patent Document 5: OPTICS EXPRESS, Vol. 3, No. 6, 14 Sep. 1998: In vivo OCT Imaging of hard and soft issue of the oral cavity

DISCLOSURE OF INVENTION

Problem to be Solved by the Invention

However, the OCT device has not been used for actual dental treatment. The use of the OCT device in dental diagnosis is not practical at least at present, and an OCT device for dental measurement does not exist as a product. This is because the OCT device requires two-dimensional (including a depth direction) mechanical scanning for obtaining one tomogram, which takes a long time for capturing an image, and in addition, the device is complicated and expensive and has poor durability.

In view of the above problem, an object of the present invention is to provide an optical coherence tomography device with a simple configuration, capable of capturing an image at a high speed.

Means for Solving Problem

In order to achieve the above object, an optical coherence tomography device according to the present invention includes: a light source; a light splitting section that splits light source light emitted from the light source into reference light with which a reference mirror is irradiated and measuring light with which a sample to be measured is irradiated; an interfering section that allows the measuring light reflected from the sample to interfere with the reference light reflected from the reference mirror to generate interference light; a photodetectiong section that measures the interference light; a measuring head that is movable by an external operation, and changes an irradiating position and/or an irradiating direction of the measuring light relative to the sample, by a motion of the measuring head; a mechanical quantity sensor that measures the motion of the measuring head in at least one direction; and an operating section that obtains information on the sample, based on the interference light measured by the photodetectiong section and the motion of the measuring head measured by the mechanical quantity sensor.

In order to achieve the above object, an optical coherence tomography device according to the present invention includes: a light source; a light splitting section that splits light source light emitted from the light source into reference light with which a reference mirror is irradiated and measuring light with which a sample to be measured is irradiated; an interfering section that allows the measuring light reflected from the sample to interfere with the reference light reflected from the reference mirror to generate interference light; a photodetectiong section that measures the interference light; an operating section that obtains information on the sample based on the interference light measured by the photodetectiong section; an optical fiber through which the measuring light passes; and a measuring head that is provided at a tip end of the optical fiber and guides the measuring light from the optical fiber to the sample, wherein the measuring head includes at least one optical axis changing section that changes a direction of an optical axis of the measuring light, and the optical axis changing section is attachable/detachable with respect to the measuring head.

Effects of the Invention

According to the present invention, an optical coherence tomography device with a simple configuration, capable of capturing an image at a high speed can be provided.

Figure 1:
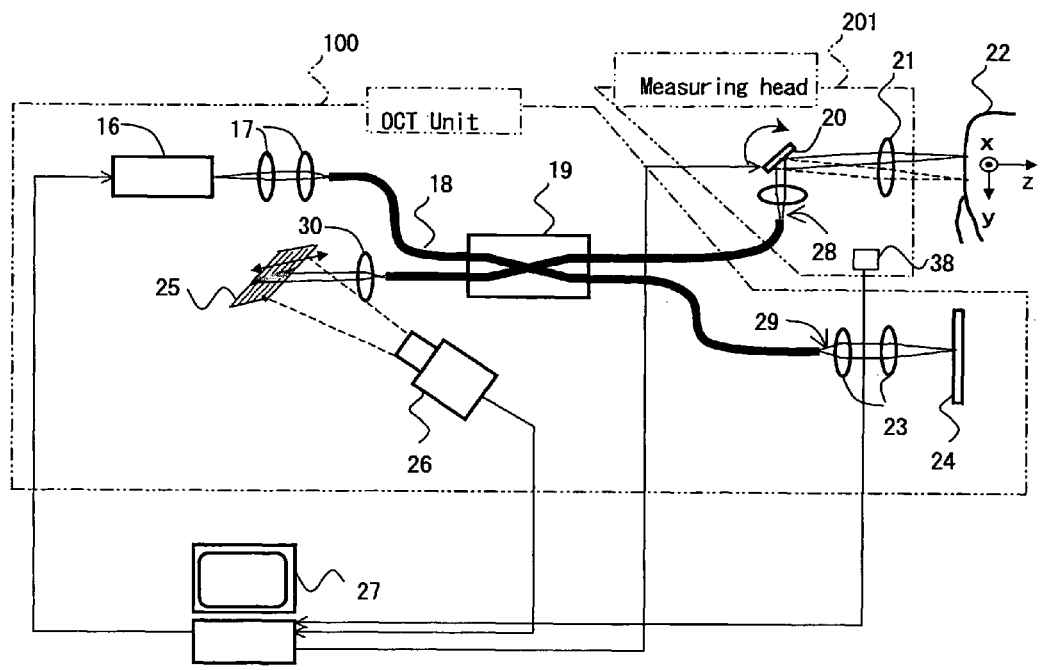
FIG. 1 is a diagram showing an example of a configuration of a Fourier domain optical coherence tomography device (hereinafter, referred to as an FD-OCT device) in Embodiment 1.

DESCRIPTION OF REFERENCE NUMERALS 1, 100, 101 OCT unit
2, 16 light source
3, 17, 23, 46 lens
4, 34 beam splitter
5, 28 measuring light
6, 29 reference light
8, 20, 49 galvanomirror
9, 12, 21 objective lens
10, 22 sample to be measured
13, 24 reference mirror
14 photodetector
18 optical fiber
19 fiber coupler
25 diffraction element
26 CCD camera
27 calculator
30 condensing lens
33 cylindrical lens
38 acceleration sensor
39 acceleration/angular velocity sensor
41 reference object
42, 43 image range
45 feature pattern
47 mirror
51 imaging range
52 switch mirror
53 rotation shaft
55 cap
57 rotation mirror
201, 202, 204, 205, 210, 211, 212, 213, 214, 215, 216 measuring head An optical coherence tomography device according to the present invention includes: a light source; a light splitting section that splits light source light emitted from the light source into reference light with which a reference mirror is irradiated and measuring light with which a sample to be measured is irradiated; an interfering section that allows the measuring light reflected from the sample to interfere with the reference light reflected from the reference mirror to generate interference light; a photodetectiong section that measures the interference light; a measuring head that is movable by an external operation, and changes an irradiating position and an irradiating direction of the measuring light relative to the sample, by a motion of the measuring head; a mechanical quantity sensor that measures the motion of the measuring head in at least one direction; and an operating section that obtains information on the sample, based on the interference light measured by the photodetectiong section and the motion of the measuring head measured by the mechanical quantity sensor.

As the mechanical quantity sensor, for example, an acceleration sensor, an angular velocity sensor, or the like can be used. As the acceleration sensor, three acceleration sensors in which sensitive axes are arranged in three respective directions orthogonal to each other can be provided. As the angular velocity sensor, three angular velocity sensors for detecting the angular velocities around an axis in three directions orthogonal to each other can be provided. Any combination of the above three acceleration sensors and the above three angular velocity sensors can be used. The mechanical quantity sensor can be selected appropriately and placed, depending upon the purpose of photographing, i.e., the measuring region of a sample and the manner in which the measuring head for capturing the measuring region moves.

For example, the measuring head is moved at least in one direction, whereby the position at which the sample is irradiated with the measuring light changes. Therefore, a plurality of sequential tomograms of the sample in the direction, or information on the sequential tomograms in the direction is obtained. On the other hand, the position at which the measuring head has moved in the direction is obtained from the acceleration measured with one acceleration sensor with a sensitive axis placed in the direction. The information on the position at which the measuring head has moved, and the sequential tomograms or the information on the sequential tomograms in the direction are obtained in synchronization, whereby information on cross-sections of wide regions of the sample in the direction is obtained even without mechanical scanning. Consequently, it is not necessary to incorporate mechanical scanning systems in a device, so that the configuration of the device becomes simple, and the device can be produced at low cost.

It is preferred that functions of the light splitting section and the interfering section are both implemented as a beam splitter or a fiber coupler.

An optical coherence tomography device according to the present invention includes: a light source; a light splitting section that splits light source light emitted from the light source into reference light with which a reference mirror is irradiated and measuring light with which a sample to be measured is irradiated; an interfering section that allows the measuring light reflected from the sample to interfere with the reference light reflected from the reference mirror to generate interference light; a photodetectiong section that measures the interference light; an operating section that obtains information on the sample based on the interference light measured by the photodetectiong section; an optical fiber through which the measuring light passes; and a measuring head that is provided at a tip end of the optical fiber and guides the measuring light from the optical fiber to the sample, wherein the measuring head includes at least one optical axis changing section that changes a direction of an optical axis of the measuring light, and the optical axis changing section is attachable/detachable with respect to the measuring head.

The measuring light passes through an optical fiber, and irradiates the sample via the measuring head provided at a tip end of the optical fiber. Therefore, the measuring head can move in accordance with the position of the sample.

The measuring head includes an optical path changing section including at least one mirror changing the irradiation direction of the measuring light. Therefore, the sample in a limited space such as an intraoral place can be photographed in various directions. Furthermore, the optical path changing section is attachable/detachable with respect to the measuring head, so that whether or not the optical path changing section is attached can be selected in accordance with the environment of the sample. Consequently, the sample in a complicated place such as an intraoral place can be photographed in various directions.

A measuring head according to the present invention is provided at a tip end of an optical fiber and guides measuring light emitted from the tip end of the optical fiber from the optical fiber to a sample to be measured. The measuring head includes at least one optical axis changing section that changes a direction of an optical axis of the measuring light, and the optical axis changing section is attachable/detachable with respect to the measuring head.

Hereinafter, embodiments of the present invention will be described with reference to the drawings.

Embodiment 1

FIG. 1 is a diagram showing an example of a configuration of a Fourier domain optical coherence tomography device (hereinafter, referred to as an FD-OCT device) in Embodiment 1.

The FD-OCT device is an OCT device characterized by detecting a spectrum obtained by diffracting interference light of measuring light reflected from a sample to be measured and reference light reflected from a reference mirror, and obtaining information on the sample in a measuring light irradiation direction from the spectrum, using Fourier inverse transform.

As shown in FIG. 1, the FD-OCT device is composed of an OCT unit 100, a measuring head 201, and a calculator 27. The OCT unit 100 is provided with a light source 16, a fiber coupler 19, a reference mirror 24, a diffraction element 25, and a CCD camera 26. The measuring head 201 is provided with a galvanomirror 20 and an objective lens 21. The calculator 27 is connected so as to communicate with the light source 16, the CCD camera 26, and the galvanomirror 20. The calculator 27 is, for example, a personal computer, and includes at least an operating section such as a CPU and a recording section such as a hard disk.

The configurations of the OCT unit 100, the measuring head 201, and the calculator 27 are not limited to those shown in FIG. 1. For example, the function of the calculator 27 can be incorporated in the OCT unit 100.

In the present embodiment, a sample 22 to be measured is a stomatognathic tissue of a living body, or an artificial composition of a stomatognathic region.

The light source 16 is low coherent in terms of time. More specifically, in the light source 16, a wavelength is distributed in a narrow range. The light source 16 is preferably a super luminescent diode, for example.

The fiber coupler 19 is an example of an optical interfering unit that performs functions of a light splitting section and an interfering section. The optical interfering unit is an input/output variable optical component that allows two input light beams to interfere with each other to output the light beams in two directions. Examples of the optical interfering unit include a beam splitter, a half mirror, and the like in addition to the fiber coupler 19.

The diffraction element 25 is a reflection-type or transmission-type optical member having a diffraction spectral function. It is preferred that the diffraction element 25 is, for example, a grating element, a diffraction grating, a prism, or the like. Furthermore, the diffraction element 25 may be a slice of an optical recording medium. Examples of the optical recording medium include a CD, a DVD, and an MO.

The CCD camera 26 is an example of a photodetectiong section. As the photodetectiong section, for example, a one-dimensional photodetector, a two-dimensional photodetector, or the like can be used. The one-dimensional photodetector is preferably a linear CCD, and the two-dimensional photodetector is preferably a CCD imaging element or a CMOS imaging element. The two-dimensional photodetector includes a two-dimensional imaging device.

The measuring head 201 preferably can be operated by an operator in a hand-held manner. Light is transmitted through an optical fiber 18 between the OCT unit 100 and the measuring head 201, whereby the movable range of the measuring head 201 is enlarged.

In the case of applying the FD-OCT device to the dental field, it is conceivable that the FD-OCD device is used on the side of a chair on which a patient is sitting during ordinary treatment. In this case, in order to position the measuring head, the entire OCT unit must be positioned orally in a patient with precision in a hollow optical system (the optical path to the measuring head is rendered hollow, instead of using an optical fiber). Furthermore, it is unrealistic that the operator operates a relatively heavy OCT unit in a hand-held manner.

The measuring head 201 can be operated by the operator in a hand-held manner, so that the operator can use the measuring head 201 easily at the side of a chair in dental treatment. The operator can use the FD-OCD device with the positional relationship between the patient and the measuring head being free.

Next, the operation of the FD-OCT device shown in FIG. 1 will be described. In the following description, a coordinate system is defined as follows. As shown in FIG. 1, it is assumed that the optical axis direction of the measuring light 28, i.e., the depth direction of the sample 22 is z, a tomographic plane is a zy-plane (realized by setting the scanning direction of the galvanomirror 20 to be y) in the sample 22, and it is assumed that directions corresponding optically to x, y, z of the sample 22 are x, y, z in a place other than the sample 22. "Corresponding optically" refers to that the light traveling direction is defined as z, the direction scanned by the galvanomirror or the like is defined as y, and the direction perpendicular to both z and y is defined as x even if a spatial direction is changed due to a mirror, a lens, an optical fiber, and the like.

The light emitted from the light source 16 is collimated by the lens 17, and thereafter, is split into reference light 29 and measuring light 28 by the fiber coupler 19. The measuring light 28 is condensed to the sample 22 by the objective lens 21 via the galvanomirror 20. Then, the measuring light 28 is scattered and reflected from the sample 22, and passes through the objective lens 21, the galvanomirror 20, the optical fiber 18, and the fiber coupler 19 again to be guided to the diffraction element 25 by a condensing lens 30.

On the other hand, the reference light 29 passes through the optical fiber 18 and a lens 23 and is reflected from the reference mirror 24. Then, the reference light 29 passes through the lens 23 again to interfere with the measuring light 28 by the fiber coupler 19, and is incident upon the condensing lens 30 in parallel with the measuring light 28 to be guided to the diffraction element 25.

The measuring light 28 and the reference light 29 are diffracted simultaneously by the diffraction element 25, and overlapped with each other in a spectrum region, thereby forming interference fringes of a spectrum (i.e., a coupling power spectrum of the measuring light 28 and the reference light 29) on the CCD camera 26. The spectrum interference fringes measured by the CCD camera 26 are subjected to Fourier inverse transform in the calculator 27, whereby a coupling correlation of the measuring light 28 and the reference light 29 is obtained. Due to the coupling correlation, the reflectance characteristics in a depth direction (z-axis direction) of the sample 22 are obtained. Information on the structure, composition, or optical characteristics in a depth direction of the sample 22 is obtained from reflectance characteristics.

Thus, it is not necessary to perform scanning in the z-axis direction by moving the reference mirror 24 to regulate the optical path length of the measuring light 28 and the optical path length of the reference light 29. More specifically, information on the structure in the depth direction (z-axis direction) of the sample 22 can be obtained without performing the mechanical operation in the z-axis direction.

In order to obtain a two-dimensional cross-sectional image of the sample 22, it is necessary to perform scanning in the y-axis direction, in addition to the z-axis direction. In the present embodiment, the scanning in the y-axis direction is performed by driving the galvanomirror 20.

As the scanning method in the y-axis direction, a method using a cylindrical lens described later, a method for driving a lens, a method for driving an optical fiber, a method for driving the sample 22, a method for allowing an operator to move the measuring head 201 (described later), and the like can be used, in addition to the method for driving the galvanomirror 20.

Herein, as a modified example of the scanning method in the y-axis direction, a method using a cylindrical lens will be described.

Figure 2:
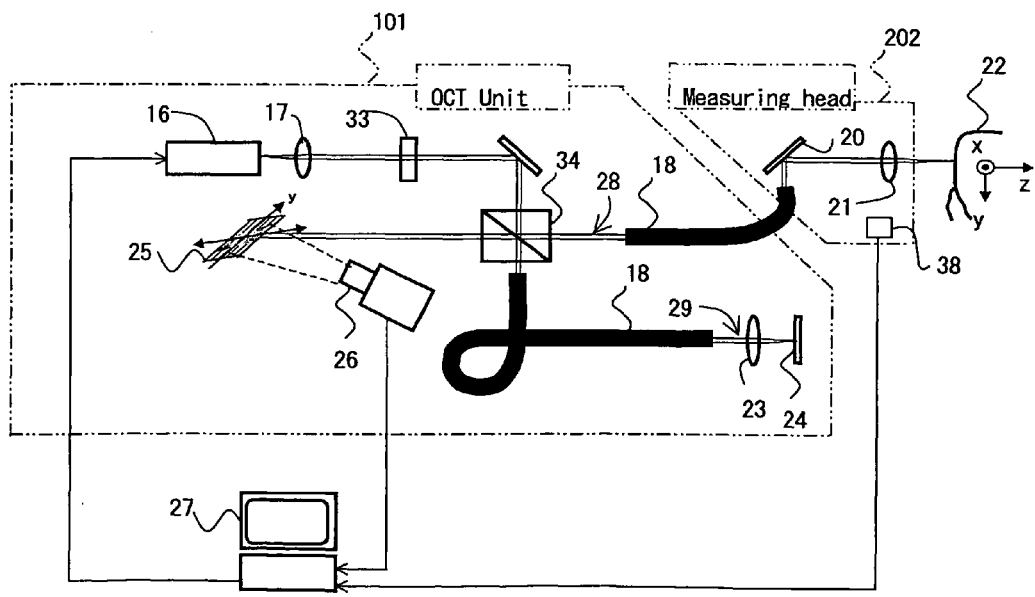
FIG. 2 is a diagram showing an example of a configuration of an FD-OCT device in Embodiment 2.

FIG. 2 is a diagram showing an example of a configuration of an FD-OCT device in which light is extended in the y-axis direction using the cylindrical lens. In FIG. 2, the same portions as those in the FD-OCT device shown in FIG. 1 are denoted with the same reference numerals as those therein, and the description thereof will be omitted.

The FD-OCT device shown in FIG. 2 is different from the FD-OCT device shown in FIG. 1 in that a cylindrical lens 33 is provided and a beam splitter 34 is used in place of the fiber coupler 19, and in the scanning direction of the galvanomirror 20.

In the FD-OCT device shown in FIG. 1, a method for driving the galvanomirror 20 is used as the scanning method in the y-axis direction. In the FD-OCT device shown in FIG. 2, the light extension in the y-axis direction by the cylindrical lens 33 is adopted in place of the scanning in the y-axis direction by the galvanomirror 20.

The cylindrical lens 33 has a direction in which the cylindrical lens 33 functions as a lens and a direction in which it does not function as a lens. The cross-section of the cylindrical lens 33 in the direction in which the cylindrical lens 33 functions as a lens and in a plane including an optical axis is the same as the cross-section of an ordinary convex lens or concave lens, and the cross-sectional shape is the same irrespective of the position in the direction in which the cylindrical lens 33 does not function as a lens. The cylindrical lens 33 is placed so that the direction in which the cylindrical lens 3 functions as a lens is in a y-direction. That is, light spread in the y-direction by the cylindrical lens 33 is distributed and radiated in the y-direction of the sample 22 (the y-direction on the cylindrical lens 33 and the y-direction of the sample 22 are identical with each other optically, and are not necessarily the same spatially). The cylindrical lens 33 functions as y-direction light-extending means. The cross-section of the measuring light 28 has a linear shape in the y-axis direction.

The function similar to that of the cylindrical lens 33 also can be realized using the cylindrical mirror.

Since the measuring light is light extended spatially in the y-axis direction, in the case where the light is guided through an optical fiber, it is necessary that the optical fiber 18 is an optical fiber with a cross-section bound in a one-dimensional line, or an optical fiber with a cross-section bound in a two-dimensional circle.

Furthermore, it is preferred that the direction of a groove of the diffraction element 25 is the y-axis direction.

The measuring light 28 is distributed and radiated in the y-axis direction of the sample 22. Therefore, the cross-section in the y-axis direction of the sample 22 can be obtained by the CCD camera 26 with one shot even without the mechanical scanning in the y-axis direction. Therefore, the galvanomirror 20 can obtain a three-dimensional structure of the sample 22 merely by the scanning in the x-axis direction.

In order to obtain a three-dimensional structure of the sample 22, it is necessary to perform the scanning in the x-axis direction in addition to the operations in the z-axis direction and the y-axis direction. In the present embodiment, a method for performing the scanning in the x-axis direction by allowing the operator to move the measuring head 201 is used.

Figure 3:
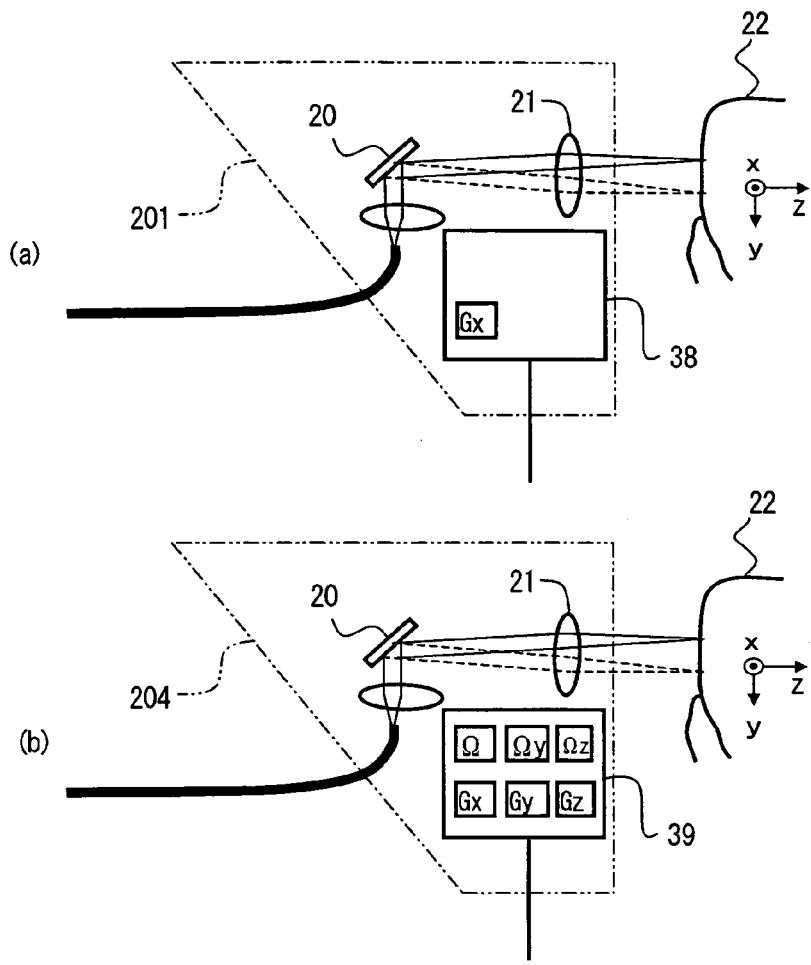
FIG. 3(a) is a diagram showing an example of a configuration of a measuring head. (b) is a diagram showing another example of a configuration of the measuring head.

FIGS. 3(a) and (b) are diagrams showing an example of a configuration of the measuring head in the present embodiment.

First, the measuring head 201 shown in FIG. 3(a) will be described.

The measuring head 201 shown in FIG. 3(a) includes an acceleration sensor 38. A sensor Gx included in the acceleration sensor 38 detects an acceleration in the x-axis direction. The measuring head 201 is movable at least in the x-axis direction with respect to the sample 22, for example, by an external operation such as an operator's operation.

When the operator moves the measuring head 201 in the x-axis direction, the position at which the sample 22 is irradiated with the measuring light 28 changes. The change in the position is obtained by integrating the accelerations detected by the acceleration sensor 38. Thus, information on the respective cross-sections of the sample 22 arranged in an x-direction is obtained, and in synchronization therewith, information from the acceleration sensor 38 is obtained, whereby the position in the x-direction of each cross-sectional information can be specified. In other words, the scanning in the x-direction can be performed when the operator moves the measuring head 201 in the x-direction. As a result, the mechanical scanning in the x-axis direction is rendered unnecessary, which makes it unnecessary to incorporate mechanical scanning means in the x-axis direction in the measuring head 201, whereby a miniaturized measuring head with a simple structure is obtained at a low cost.

The acceleration sensor 38 is connected to the calculator 27 (see, for example, FIG. 1), and data detected by the acceleration sensor is sent to the calculator 27.

Two acceleration sensors: the acceleration sensor in the x-direction and the acceleration sensor in the y-direction may be attached to the measuring head 201. Even in the case where the operator moves the measuring head 201 in the y-direction, the position in the y-direction of each cross-sectional information can be specified based on each cross-sectional information of the sample 22 arranged in the y-direction and information on the acceleration sensor in the y-direction synchronized therewith, in the same way as in the case where the measuring head 201 is moved in the x-direction. In this case, the scanning in the y-axis direction by the galvanomirror 20 or the light extension in the y-direction by the cylindrical lens 33 can be omitted.

In the FD-OCT device according the present embodiment, as described above, the structure in the z-axis direction of the sample 22 is obtained from spectrum interference fringes. The scanning in the y-axis direction or the x-axis direction can be performed by moving the measuring head 201. Therefore, the incorporation of the mechanical scanning means in the device can be omitted. As a results, the configuration of the device is simplified, and high-speed imaging can be performed.

Next, a measuring head 204 shown in FIG. 3(b) will be described. The measuring head 204 is a modified example of the measuring head 201.

The measuring head 204 shown in FIG. 3(b) includes an acceleration/angular velocity sensor 39. The acceleration sensor 39 includes acceleration sensors $G_x$, $G_y$, $G_z$ for detecting accelerations in the x, y, and z-axis directions, respectively, and angular velocity sensors $\Omega_x$, $\Omega_y$, $\Omega_z$ for detecting angular velocities around x, y, and z-axes. The measuring head 204 is movable with respect to the sample 22 by an external operation such as an operator's operation. Furthermore, the acceleration/angular velocity sensor 39 is connected to the calculator 27, and data detected by the acceleration/angular velocity sensor 39 is sent to the calculator 27.

The acceleration/angular velocity sensor 39 is provided at the measuring head 204, whereby respective spatial positions/directions of a plurality of measurement cross-sections measured by the measuring head 204 during movement can be specified, with respect to any movement of the measuring head 204 by the operator. As a result, three-dimensional data containing the internal structure of the sample 22 can be obtained in a range in which the measuring head 204 has moved. In this case, the scanning in the x-axis and y-axis directions by the galvanomirror 20 can be omitted.

Hereinafter, an example of a flow of the processing of obtaining three-dimensional data on the sample 22 will be described.

At commencement of the measurement, information on position/direction is reset in the calculator 27. An initial tomogram is obtained simultaneously with the reset, and the plane of a cross-sectional image is defined as a zy-plane on x=0, the depth direction of the tomogram is defined as a z-direction, the horizontal direction is defined as a y-direction, and the center of the tomogram is defined as y=0 and z=0.

The movement of the measuring head 204 thereafter is obtained as position/direction data of the measuring head 204 by subjecting the output of the acceleration sensor to time quadrature twice in the calculator 27 and subjecting the output of the angular velocity sensor to time quadrature once in the calculator 27. The position/direction data on the measuring head 204 is saved in synchronization with the cross-sectional image data obtained when the measuring head 204 has moved.

The calculator 27 calculates the position/direction of a tomogram after the reset from the position/direction data of the measuring head 204, and each tomogram data is synthesized spatially, whereby three-dimensional data containing the internal structure of the sample 22 is constructed.

In the calculator 27, data processing regarding the three-dimensional data on the sample 22 (for example, the extraction of a tissue, the specification of a lesion, data analysis, etc.) is conducted, and the processing results are saved.

Furthermore, the calculator 27 also can display the connection of measurement cross-sections, any cross-section, arrangement of measurement cross-sections, a stereoscopic surface, a combination thereof, or the like on a monitor.

According to the present embodiment, the three-dimensional movement of the measuring head 204 at a time of OCT measurement is detected by the acceleration/angular velocity sensor 39 provided at the measuring head 204, whereby the six-degree-of-freedom on a three-dimensional space of measuring region data containing internal information on the sample 22 can be positioned.

Furthermore, the imaging range of the OCT device including the FD-OCT device is limited to several mm×several mm even if mechanical scanning of the galvanomirror or the like is performed. In contrast, for example, in an oral tissue and a peripheral tissue thereof, the imaging range of one tooth is 5 to 15 mm. The imaging range of one tooth and a periodontal tissue is 20 mm, and the imaging range of a dental arch is 100 to 150 mm.

Even in the FD-OCT device in which a tomogram is obtained by scanning or extension in the x-axis or y-axis direction using the galvanomirror, the cylindrical lens, and the like, the width of the tomogram is only several mm, and if we measure the width of a tomogram in a region exceeding several mm, it is necessary to measure separately at least twice.

Therefore, in most cases, it is necessary to obtain a plurality of tomograms arranged in the y-direction by a plurality of measurements, and the positional relationship of "a plurality of arranged tomogram data" needs to be obtained. According to the present embodiment, the three-dimensional position/direction relationship of a plurality of arranged tomograms is clarified, so that the measurement data in a wide range can be constructed. Furthermore, the three-dimensional position and direction relationships of a plurality of tomograms can be specified.

Furthermore, the basic characteristics of the OCT device in which three-dimensional internal information on a sample to be measured can be obtained quantitatively, and the excellent characteristics such as noninvasiveness and high resolution can be exhibited, for example, in the dental field.

In the present embodiment, the FD-OCT device has been described. However, the present invention is not limited to the FD-OCT device, and may be an OCT device that is not an FD-OCT device. For example, a simple mirror may be used in place of the diffraction element 25, and the CCD camera 26 may be a photodetector.

Embodiment 2

In an FD-OCT device in Embodiment 2, portions of the FD-OCT device shown in FIG. 1 or 2 other than those described below can be applied, so that the description thereof will be omitted.

In the FD-OCT device in the present embodiment, the calculator 27 (see, for example, FIG. 1) performs positioning on a three-dimensional space of information on the sample 22, measured by the measuring head. In the present embodiment, the sample 22, having a reference object 41 whose shape previously is known, is measured.

Figure 4:
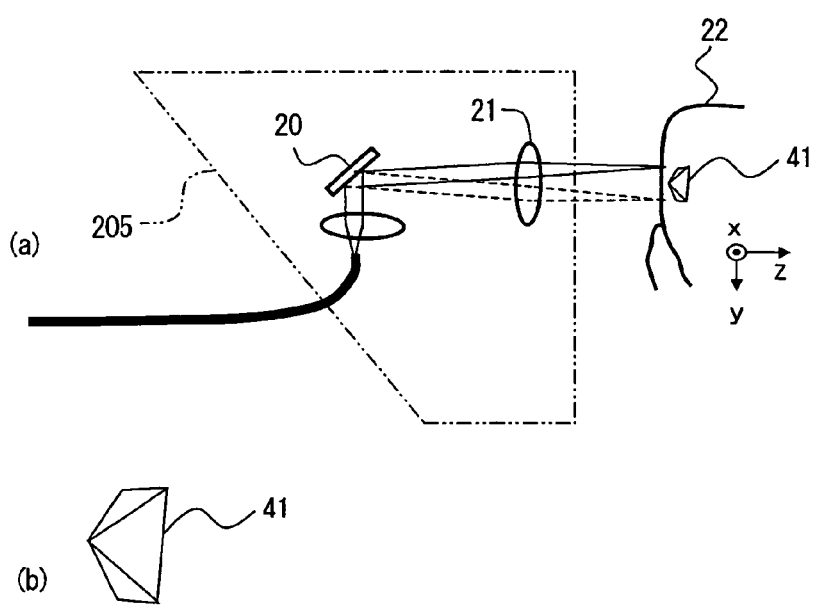
FIG. 4(a) is a diagram showing an example in which a reference object 41 is attached to a sample 22. (b) is a view showing an example of the reference object 41.

FIG. 4(*a*) is a diagram showing an example in which the reference object 41 is attached to the sample 22. FIG. 4(*b*) is a diagram showing an example of the reference object 41. It is assumed that the position and direction of any cross-section of the reference object 41 can be specified. It is preferred that the reference object 41 is a quadrangular pyramid. A flow of the following processing will be described.

At a commencement of measurement, the position/direction information is reset in the calculator 27. An initial tomogram containing the reference object 41 whose shape is previously known is obtained simultaneously with the reset, and a coordinate system of the sample 22 based on the reference object 41 is determined.

After that, the tomogram obtained by moving the measuring head 205 also is measured together with the reference object 41, and the position/direction of a tomogram is calculated based on the position/direction of the reference object 41 in the calculator 27. The respective tomogram data are synthesized spatially to construct three-dimensional data containing the internal structure of the sample 22.

In the above processing, the FD-OCT device measured the sample 22 while fixing the reference object 41 whose shape is previously known to the sample 22 before performing the OCT measurement operation. A method shown below, which is a different method from the above, also can be used.

After the OCT measurement operation along with the movement of the measuring head for obtaining data of a plurality of or continuous OCT tomogram, the entirety or part of a measured sample is specified from the obtained data as reference shape, and the shape of the measured samples represented in the obtained data is matched with the reference shape, whereby the 6-degree-of-freedom on a three-dimensional space of a plurality of or continuous OCT tomogram data of the sample can be positioned.

In the present embodiment, the FD-OCT device has been described. However, the present invention is not limited to the FD-OCT device, and may be an OCT device that is not an FD-OCT device.

Embodiment 3

In an OCT device in Embodiment 3, portions of the FD-OCT device shown in FIG. 1 or 2 other than those described below can be applied, so that the description thereof will be omitted.

In the FD-OCT device in the present embodiment, a tomogram of the sample 22, measured by the FD-OCT device, is positioned on a three-dimensional space. In the present embodiment, a common data structure is extracted from a plurality of measuring region data containing the internal information on the sample 22, whereby the positional relationship of the 6-degree-of-freedom on the three-dimensional space of the measuring region data is determined.

Figure 5:
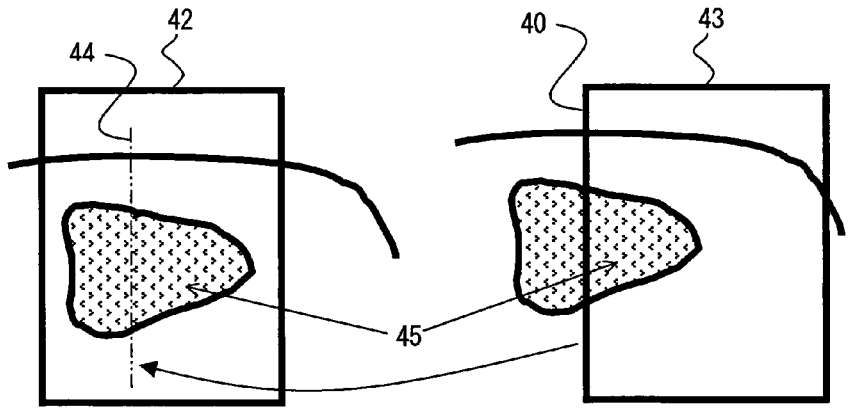
FIG. 5 is a diagram showing an image in a plurality of measuring region data.

FIG. 5 is a diagram showing an image in a plurality of measuring region data. An image range 42 is a certain cross-sectional image of the sample 22 obtained in the FD-OCT device. An image range 43 is a cross-sectional image in the case where a measuring region different from the measuring region in the image range 42 is measured, for example, by the movement of the measuring head or the like. A flow of the following processing will be described.

At a time of commencement of measurement, the position/direction is reset in the calculator 27 (see, for example, FIG. 1). A cross-section of the sample 22 is measured at a time of the reset. It is assumed that the cross-sectional image obtained by the measurement at a time of the reset is the image range 42. A feature pattern 45 is extracted from the image range 42. The feature pattern is, for example, an image of a lesion contained in the sample 22.

After that, a measuring region different from that in the image range 42 is measured, for example, by the movement of the measuring head or the like. A cross-sectional image obtained at that time is assumed to be the image range 43. The calculator 27 extracts the feature pattern 45 from the image range 43. A series of measurements are performed uncontinuously or continuously while the measuring head is being moved. Therefore, the position of the feature pattern can be tracked by continuing the operation.

The calculator 27 connects respective images, matching the feature pattern 45 in the image range 42 and the feature pattern in the image range 43. In the case shown in FIG. 5, a left side 40 of the image range 43 can be connected so as to be aligned with the position represented by a chain double-dashed line 44 in the image range 42.

The calculator 27 performs the above image connection processing with respect to a plurality of images, thereby constructing data in a wide range containing the internal structure of the sample 22.

In the present embodiment, the FD-OCT device has been described. However, the present invention is not necessarily limited to the FD-OCT device, and may be an OCT device that is not an FD-OCT device.

Embodiment 4

FIGS. 6-12 are diagrams showing a configuration of the measuring head of the OCT device in Embodiment 4. In an OCT device in the present embodiment, portions of the FD-OCT device shown in FIG. 1 or 2 or the conventional OCT device, other than those described below, can be applied, so that the description thereof will be omitted.

Figure 6:
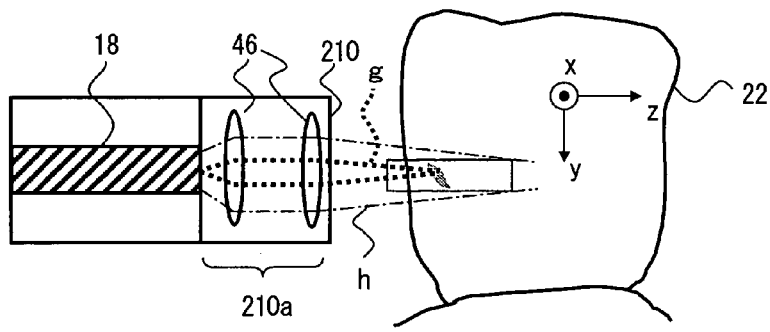
FIG. 6 is a diagram showing a preferred example of a configuration of a measuring head.

FIG. 6 is a diagram showing a preferred example of a configuration of the measuring head of the OCT device in the present embodiment.

In the example shown in FIG. 6, a measuring head 210 is provided at a tip end of the optical fiber 18. The optical fiber guides measuring light emitted from a light splitting section (for example, the beam splitter 34) of the OCT unit 101 (see, for example, FIG. 2) to the sample 22, and guides the measuring light reflected from the sample 22 to an interfering section (for example, the beam splitter 34) of the OCT unit 101 again.

The measuring head 210 is preferably used as a measuring head of an FD-OCT device of the type using a cylindrical lens, for example, as in the FD-OCT device shown in FIG. 2. The optical fiber 18 is a bundle, and measuring light spread in the y-direction is distributed and radiated in the y-direction of the sample 22 from the optical fiber 18. In FIG. 6, a dotted line g represents a center image-forming light beam, and alternate long and short dashed lines h represent an imaging area.

In the measuring head 210, a portion extending forward from the tip end of the optical fiber 18 is a radiating and condensing section 210a. The radiating and condensing section 210a collimates the measuring light through the lens 46 without changing the optical axis direction with respect to the optical axis direction of the optical fiber at the optical fiber tip end portion, and irradiates the sample 22 with the measuring light. Furthermore, the radiating and condensing section 210a condenses reflected light in the z-direction from the sample 22.

Figure 7:
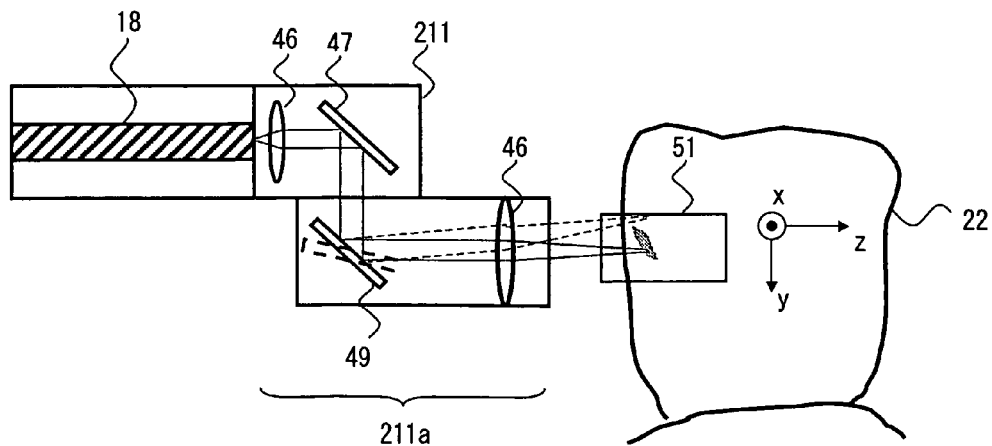
FIG. 7 is a diagram showing another preferred example of a configuration of the measuring head.

FIG. 7 is a diagram showing another preferred example of a configuration of the measuring head of the OCT device in the present embodiment.

In the example shown in FIG. 7, a radiating and condensing section 211a changes the optical axis direction of the measuring light to a direction different from the optical axis direction of the optical fiber 18 in the tip end portion of the optical fiber 18, with a mirror 49 (galvanomirror) fixed to the radiating and condensing section 211a and driven for scanning and a mirror 47 (fixed mirror) that is not driven for scanning. That is, the galvanomirror 49 and the mirror 47 function as optical axis changing sections.

The measuring head 211 can be used as a measuring head of an FD-OCT device of the type including the galvanomirror, for example, as in the FD-OCT device shown in FIG. 1. The number of the optical fiber 18 is one, and the measuring light output from the optical fiber 18 is scanned in the y-axis direction by the galvanomirror 49. More specifically, the galvanomirror 49 rotates, whereby an image-forming point in the sample to be measured moves in an imaging range 51.

Measuring heads 210 and 211 shown in FIGS. 6 and 7 are effective for measuring a tomogram of a foretooth, an eyetooth, and a front molar from a buccal plane.

FIG. 8(a) is a diagram showing still another preferred example of a configuration of the measuring head of the OCT device in the present embodiment.

A measuring head 212 can be used as a measuring head of an FD-OCT device of the type using a cylindrical lens, for example, as in the measuring head of the OCT device shown in FIG. 2. The optical fiber 18 is a bundle, and measuring light spread in the y-direction is distributed and radiated from the optical fiber 18 in the y-direction of the sample 22. In FIG. 8(a), a dotted line g represents a center image-forming light beam, and alternate long and short dashed lines h represent an imaging area.

The radiating and condensing section 212a changes the optical axis direction of measuring light by the mirror 47 that is fixed and is not driven for scanning.

FIG. 8(b) is a diagram showing still another preferred example of a configuration of the measuring head of the OCT device in the present embodiment.

A measuring head 213 can be used as a measuring head of an FD-OCT device of the type including a galvanomirror, for example, as in the FD-OCT device shown in FIG. 1. The number of the optical fiber 18 is one, and the measuring light output from the optical fiber is scanned in the y-axis direction by the galvanomirror 49.

In the example shown in FIG. 8(b), the radiating and condensing section 213a changes the optical axis direction of the measuring light with respect to the optical axis direction of the optical fiber 18 in a tip end portion of the optical fiber 18, by the mirror (galvanomirror) 49 that is fixed to the radiating and condensing section 213a and driven for scanning.

The measuring heads 212, 213 shown in FIGS. 8(a) and 8(b) are effective for measuring a tomogram from an occlusal surface of teeth. The measuring heads 212, 213 shown in FIGS. 8(a) and 8(b) also are effective for measuring a tomogram of lingual surface of a molar portion, in addition to the clenched plane.

Figure 9:
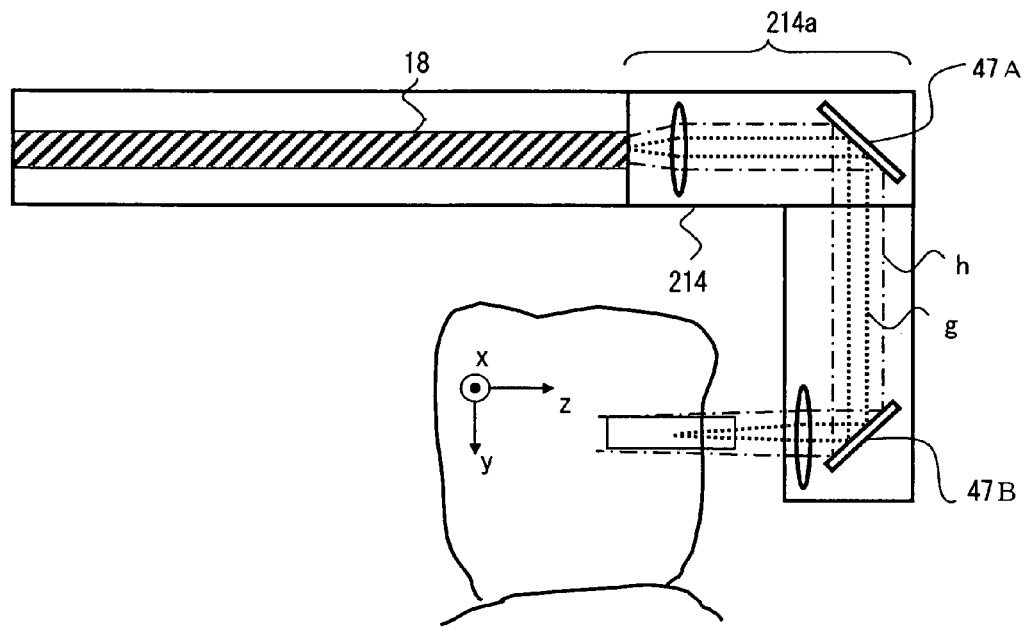
FIG. 9 is a diagram showing another preferred example of a configuration of the measuring head.

FIG. 9 is a diagram showing still another preferred example of a configuration of the measuring head of the OCT device in the present embodiment.

The measuring head 214 can be used as a measuring head of an FD-OCT device of the type using a cylindrical lens, for example, as in the measuring head of the OCT device shown in FIG. 2. The optical fiber 18 is a bundle, and measuring light spread in the y-direction is distributed and radiated from the optical fiber 18 in the y-direction of the sample 22. In FIG. 9, a dotted line g represents a center image-forming light beam, and alternate long and short dashed lines h represent an imaging area.

A radiating and condensing section 214a changes the optical axis direction of the measuring light by two mirrors 47A and 47B that are fixed to a radiating and condensing section 214a and are not driven for scanning. The radiating and condensing section 214a can realize an L-shape. That is, there is an open space in which a tooth germ that is the sample 22 can be placed in the L-shape.

Figure 10:
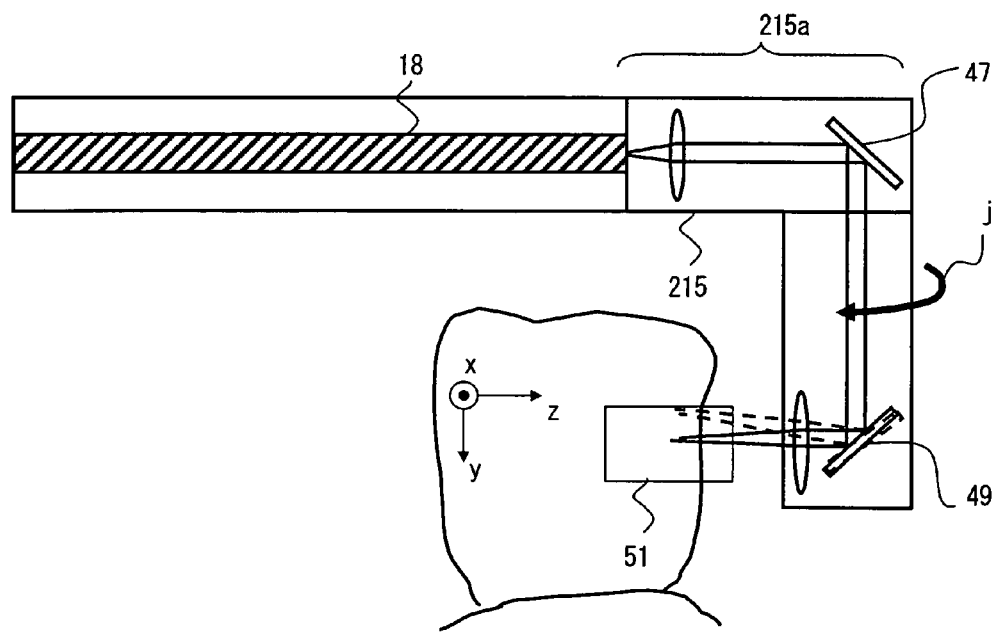
FIG. 10 is a diagram showing another preferred example of a configuration of the measuring head.
Figure 11:
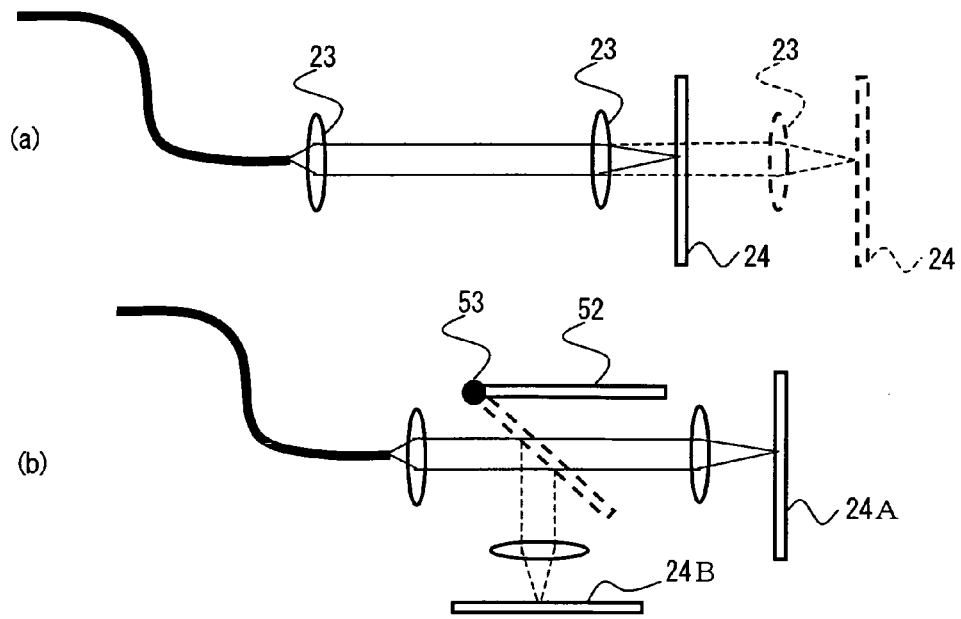
FIG. 11(a) is a diagram showing an example in the case where the position of a reference mirror is switched. (b) is a diagram showing an example of a configuration in which a reference mirror for reflecting reference light is switched among a plurality of reference mirrors at different positions.

FIG. 10 is a diagram showing still another preferred example of a configuration of the measuring head of the OCT device in the present embodiment.

The measuring head 215 can be used as a measuring head of an FD-OCT device of the type including the galvanomirror, for example, as in the FD-OCT device shown in FIG. 1. The number of the optical fiber 18 is one, and the measuring light output from the optical fiber 18 is scanned in the y-axis direction by the galvanomirror 49.

In the example shown in FIG. 10, a radiating and condensing section 215a changes the optical axis direction of the measuring light by the mirror (galvanomirror) 49 that is driven for scanning and the mirror 47 that is not driven for scanning. The radiating and condensing section 215a realizes an L-shape, and has an open space in which a tooth germ that is the sample 22 can be placed in the L-shape.

The measuring heads 214 and 215 shown in FIGS. 9 and 10 are effective for measuring a tomogram from a lingual surface of a tooth.

In the measuring heads 210 to 215 shown in FIGS. 6 to 13, it is preferred that at least a part of the radiating and condensing sections 210a to 215a can be separated from the tip end portion of the optical fiber 18 or the OCT unit, and can be replaced.

Furthermore, it is preferred that at least a part of the measuring heads 210 to 215 shown in FIGS. 6 to 13 can rotate. For example, the tip end portion of the measuring head 215 shown in FIG. 10 can be set to be rotatable in the direction of an arrow j. Furthermore, a mirror of the radiating and condensing section of the measuring head closest to a subject can be rendered rotatable.

Hereinafter, an example of the case where at least a part of the radiating and condensing sections 210a to 215a is separated or replaced in the measuring heads 210 to 215 will be described.

Figure 8:
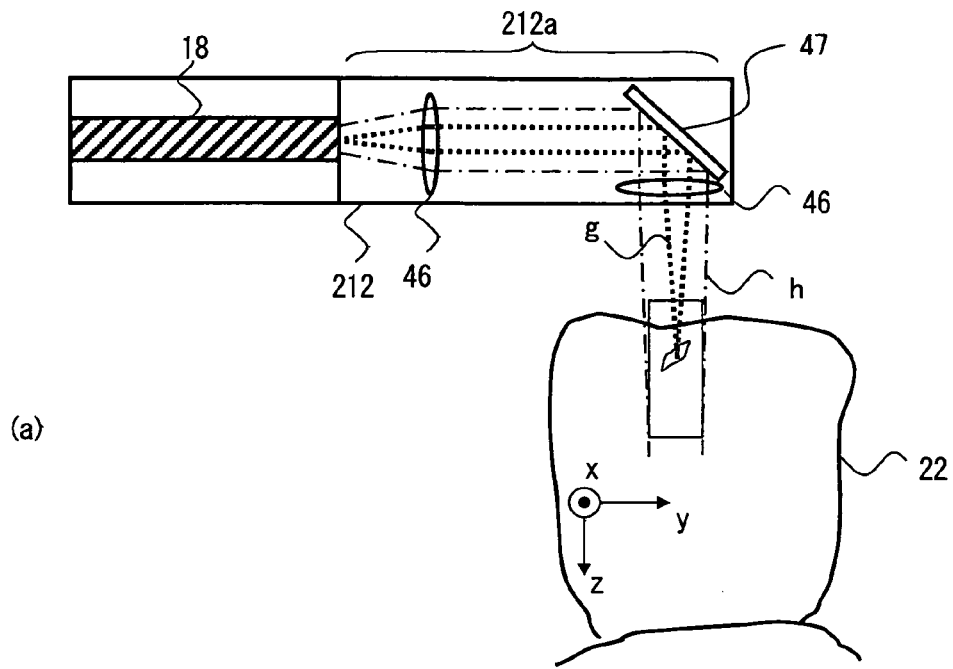
FIG. 8(a) is a diagram showing another preferred example of a configuration of the measuring head. (b) is a diagram showing still another preferred example of a configuration of the measuring head.
Figure 8:
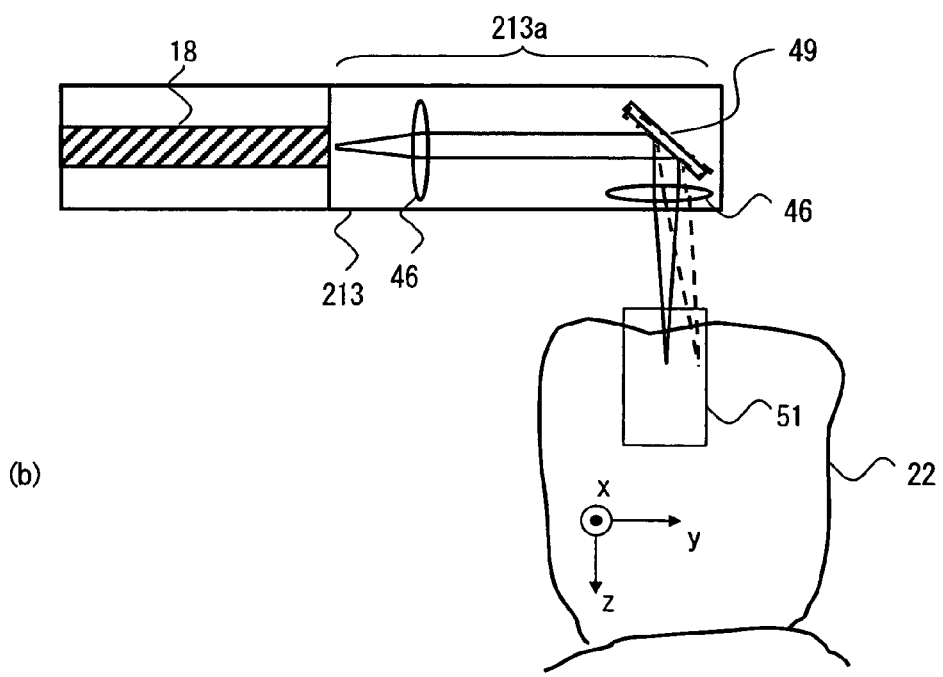

For example, in the case where the radiating and condensing section 210a shown in FIG. 6 is removed and replaced by the radiating and condensing section 212a shown in FIG. 8, the optical distance of the measuring light in the radiating and condensing section becomes long. However, in the OCT device, the optical distance of the measuring light needs to be substantially matched with the optical distance of reference light. Therefore, when the optical distance of the measuring light is changed, it also is necessary to change the optical distance of the reference light accordingly. More specifically, it is necessary to change the optical distance of reference light so that the optical distance from the light splitting section (interfering section) of the beam splitter 34 or the fiber coupler 19 to a substantially central position of the measuring range is equal to the optical distance from the light splitting section (interfering section) to the reference mirror.

Regarding the method for changing the optical distance of reference light, it is preferred that the position of a reference mirror is changed, or the reference mirror for reflecting reference light is switched among a plurality of reference mirrors at different positions.

FIG. 11(a) is a diagram showing an example of the case where the position of the reference mirror is switched. The positions of the reference mirror 24 and the lens 23 are switched between the positions represented by a solid line and the positions represented by a dotted line. This switch can be performed by a linear actuator or manually. In FIG. 11(a), two respective positions of the reference mirror 24 and the lens 23 are represented by a solid line and a dotted line. The position of the reference mirror 24 may be switched at three or more positions having different optical distances by providing three or more stop positions for the reference mirror 24 and the lens 23.

FIG. 11(b) is a diagram showing an example of a configuration in which the reference mirror for reflecting reference light is switched among a plurality of reference mirrors at different positions. In the configuration shown in FIG. 11(b), two reference mirrors 24A and 24B having different reference optical path lengths are provided. The switch between these two reference mirrors 24A and 24B is performed by a switch mirror 52. The switch mirror 52 rotates by about 45° with an end thereof as a rotation axis 53. The switch mirror 52 is rotated by a motor or manually. In FIG. 11(b), the angle and an optical path to be switched of the switch mirror 52 are represented by a solid line and a broken line. The reference mirror 24 also can be switched at three or more positions having different optical distances by providing three or more stop angles for the switch mirror 52. A plurality of lenses for forming an image may be provided at the reference mirror 24 together with the reference mirror 24.

Furthermore, even in the case where any two of the radiating and condensing sections 210a to 215a are switched, the radiating and condensing sections 210a to 215a can be designed so that the optical distance of measuring light does not change. More specifically, the optical axis changing sections such as the mirror 47 and the galvanomirror 49 also can be placed so that the optical distances of the measuring light of the radiating and condensing sections 210a to 215a become equal to each other. Furthermore, the optical distance of measuring light can be adjusted by providing an optical fiber in the radiating and condensing sections 210a to 215a.

For example, in the measuring head 211 shown in FIG. 7, the distance between the mirror 47 and the galvanomirror 49 can be set so that the optical distance of measuring light becomes equal to the optical distance of measuring light in the measuring head 213 shown in FIG. 8(b) and the measuring head 215 shown in FIG. 10.

The configuration in which the measuring head is inserted orally is conceivable. When the measuring head is inserted orally, the measuring head may come into contact with a tooth germ. Thus, it is necessary to sterilize or dezymotize the measuring head. Therefore, it is preferred that a covering such as a cap or a cover made of a material capable of transmitting measuring light (z-direction object reflected light) can be attached to the tip end of the measuring head.

Figure 12:
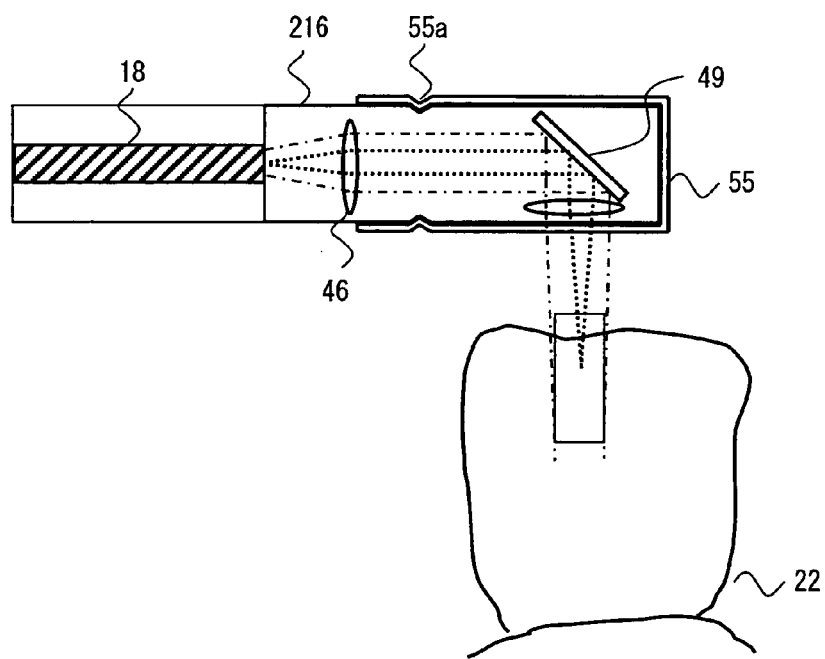
FIG. 12 is a diagram showing an example in the case where a cap for sterilization is attached to a measuring head.
Figure 13:
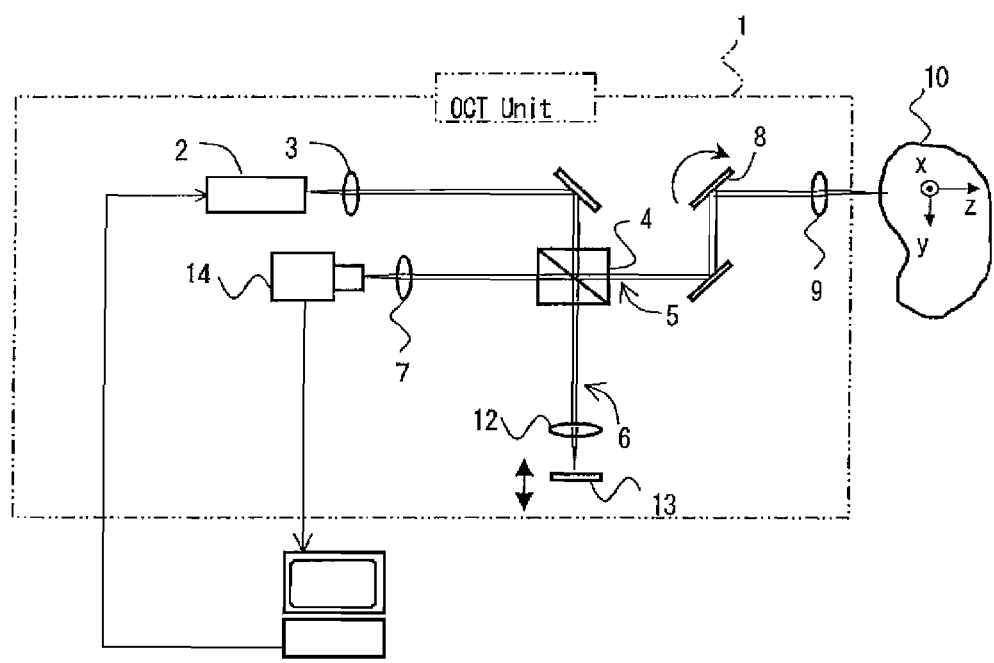
FIG. 13 is a diagram showing a configuration of a conventional OCT device.

FIG. 12 is a diagram showing an example in the case where the cap for sterilization is attached to the measuring head. As shown in FIG. 12, a cap 55 is attached to the tip end portion of the measuring head 216. The cap 55 includes a restriction 55a for being fixed to the measuring head 216. A housing of the measuring head 216 also is provided with a restriction corresponding to the restriction 55a of the cap 55.

It is necessary that the cap 55 and the measuring head 216 can be sterilized. Therefore, it is preferred to use a material that has heat resistance at a temperature of 100° C. to 150° C. or a material that is not denatured or deformed with gas for sterilization, for the constituent members of the measuring head 216. It is preferred to use a material that does not change the optical property of measuring light except for intensity and a wavelength, for the cap 55. Furthermore, it is preferred to use a material that is known regarding the influence of a phase/polarization state. The cap is preferably made of a transparent material and disposable. Preferred examples of the material include glass, a resin, and ceramics. They are not necessarily required to be transparent to visible light as long as they transmit measuring light.

As described above, a sample to be measured can be measured by an OCT device, which has been difficult to be measured conventionally, by using the measuring head according to the present embodiment. For example, teeth are arranged in a complicated manner, and respective teeth planes have various angles and directions. This also varies greatly depending upon the individual. If planes directed in these various directions are measured by a measuring head inserted through an opening such as an oral cavity, it is necessary to direct the hand holding the measuring head in various directions so as to irradiate a tooth plane with measuring light perpendicularly. In the conventional OCT device, in most cases, a patient may have inappropriate posture, and it may be impossible to irradiate a tooth plane desired to be irradiated with measuring light perpendicularly. According to the measuring head of the present embodiment, a tooth plane can be irradiated with measuring light perpendicularly, with respect to a teeth row in the oral cavity from various directions

INDUSTRIAL APPLICABILITY

The present invention is applicable as an inexpensive optical coherence tomography device with a simple structure, capable of performing high-speed measurement, in particular, a device for dental measurement.

The invention claimed is:

1. An optical coherence tomography device, comprising:
    a light source;
    a light splitting section that splits light source light emitted from the light source into reference light with which a reference mirror is irradiated and measuring light with which a sample to be measured is irradiated;
    an interfering section that allows the measuring light reflected from the sample to interfere with the reference light reflected from the reference mirror to generate interference light;
    a photo detecting section that measures the interference light;
    a measuring head that is movable by an external operation, and changes at least an irradiating position and/or an irradiating direction of the measuring light relative to the sample, by a motion of the measuring head;
    a mechanical quantity sensor that measures the motion of the measuring head in at least one direction; and
    an operating section that obtains information on a reflectance distribution in a depth direction inside the sample, obtained from the interference light measured by the photodetecting section, and information indicating a position of the reflectance distribution, obtained from the motion of the measuring head measured by the mechanical quantity sensor, in synchronization with the information on the reflectance distribution, and the operating section constructs an image inside the sample based on the information on the reflectance distribution and the information indicating the position of the reflectance distribution.

2. The optical coherence tomography device of claim 1, wherein the operating section obtains information on a continuous reflectance distribution connected in a movement direction of the measuring head.

3. The optical coherence tomography device of claim 1, wherein the information on a reflectance distribution contains information on a reflectance distribution of a reference object which is attached to the sample and whose shape is known previously, and
    the operating section calculates the information indicating a position of the reflectance distribution based on the information on the reflectance distribution of the reference object, and constructs an image inside the sample based on the obtained position and the information on the reflectance distribution.

4. The optical coherence tomography device of claim 1, wherein the operating section extracts a feature pattern in the image obtained from the information on the reflectance distribution, connects a plurality of images based on the feature pattern, and constructs an image inside the sample.

* * * * *